United States Patent
Chen et al.

(10) Patent No.: US 11,944,659 B2
(45) Date of Patent: Apr. 2, 2024

(54) **METHOD FOR IMPROVING SARCOPENIA BY USING *PHELLINUS LINTEUS***

(71) Applicant: GRAPE KING BIO LTD, Taiwan (CN)

(72) Inventors: Chin-Chu Chen, Taiwan (CN); I-Chen Li, Taiwan (CN); Tsung-Ju Li, Taiwan (CN); Ting-Yu Lu, Taiwan (CN); Yen-Po Chen, Taiwan (CN)

(73) Assignee: GRAPE KING BIO LTD, Taiwan (CN)

( * ) Notice: Subject to any disclaimer, the term of this patent is extended or adjusted under 35 U.S.C. 154(b) by 151 days.

(21) Appl. No.: 17/499,261

(22) Filed: Oct. 12, 2021

(65) Prior Publication Data

US 2022/0118037 A1 Apr. 21, 2022

(30) Foreign Application Priority Data

Oct. 19, 2020 (TW) .............................. 109136177

(51) Int. Cl.
| | | |
|---|---|---|
| *A61K 36/07* | (2006.01) | |
| *A23K 50/50* | (2016.01) | |
| *A23L 31/00* | (2016.01) | |
| *A23L 33/10* | (2016.01) | |
| *A61P 21/06* | (2006.01) | |
| *B01D 11/02* | (2006.01) | |

(52) U.S. Cl.
CPC .............. *A61K 36/07* (2013.01); *A23K 50/50* (2016.05); *A23L 31/00* (2016.08); *A23L 33/10* (2016.08); *A61P 21/06* (2018.01); *B01D 11/0288* (2013.01); *A23V 2002/00* (2013.01); *A61K 2236/11* (2013.01); *A61K 2236/333* (2013.01); *A61K 2236/37* (2013.01)

(58) Field of Classification Search
None
See application file for complete search history.

(56) References Cited

FOREIGN PATENT DOCUMENTS

| | | |
|---|---|---|
| CN | 1636547 A | 7/2005 |
| CN | 101011428 A | 8/2007 |
| CN | 101182550 A | 5/2008 |
| CN | 101474211 A | 7/2009 |
| CN | 108697685 A | 10/2018 |
| CN | 109680017 A | 4/2019 |
| JP | 2002171936 A | 6/2002 |
| JP | 2018521118 A | 8/2018 |
| KR | 20190079848 A | 7/2019 |
| TW | 200825177 A | 6/2008 |
| TW | 201601737 A | 1/2016 |
| TW | I729928 B | 6/2021 |

OTHER PUBLICATIONS

Revilla et al. (1998) J. Agric. Food Chem. 46: 4592-4597. (Year: 1998).*
Raskin et al. (2004) Current Pharmaceutical Design 10, 3419-3429. (Year: 2004).*
Jin-Hee Seo, "Effects of Phellinus Linteus Administration on Serotonin Synthesis in the Brain and Expression of Monocarboxylate Transporters in the Muscle during Exhaustive Exercise in Rats", Journal, 2011, 95-103, vol. 57, Journal of Nutritional Science and Vitaminology.
Jun Myoung Park, "Cytoprotective Effect of Hispidin against Palmitate-Induced Lipotoxicity in C2C12 Myotubes", Journals, 2015, 5456-5467, vol. 20, Molecules.
Xiang Lang Sang Huang, "The nine main detection results of Phellinus linteus of wild mulberry in Shennongjia are stunning", http://www.360doc.com/content/19/0813/20/65375620_854678872.shtml, Aug. 13, 2019. (with its English translation of the relevant part).

* cited by examiner

*Primary Examiner* — Russell G Fiebig
(74) *Attorney, Agent, or Firm* — Hayes Soloway PC

(57) ABSTRACT

The invention provides a method for improving sarcopenia of a subject in need thereof by using *Phellinus linteus*, in which the method includes administering an effective dose of composition to the subject, and the composition includes *Phellinus linteus* (NITE BP-03321 and BCRC 930210) as an effective substance. By using the aforementioned composition including an extract of a fermented product of the *Phellinus linteus* and/or its derivative, diameters of myotubes, amounts of muscles and muscle muscular endurance can be maintained, thereby improving sarcopenia.

8 Claims, 3 Drawing Sheets

100 μm

100 μm

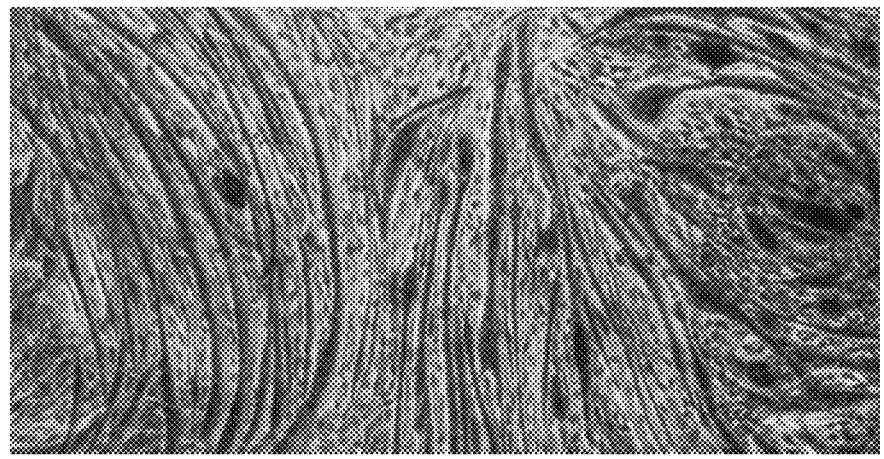
FIG. 1C  100 μm
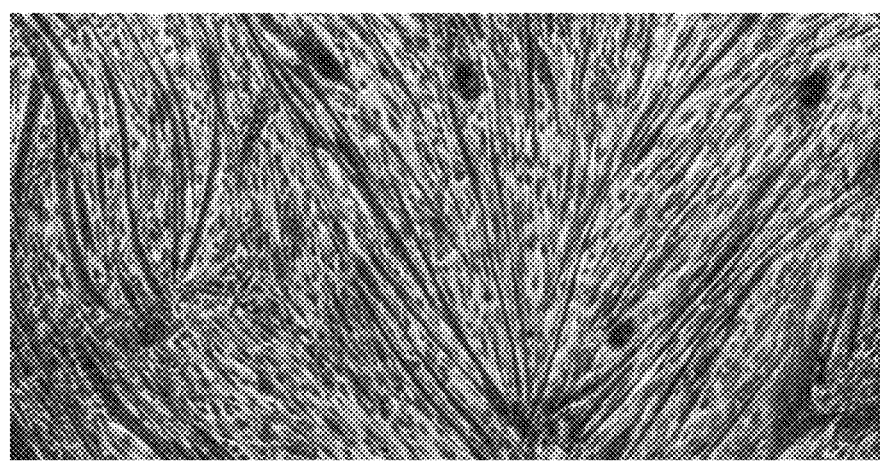
FIG. 1D  100 μm

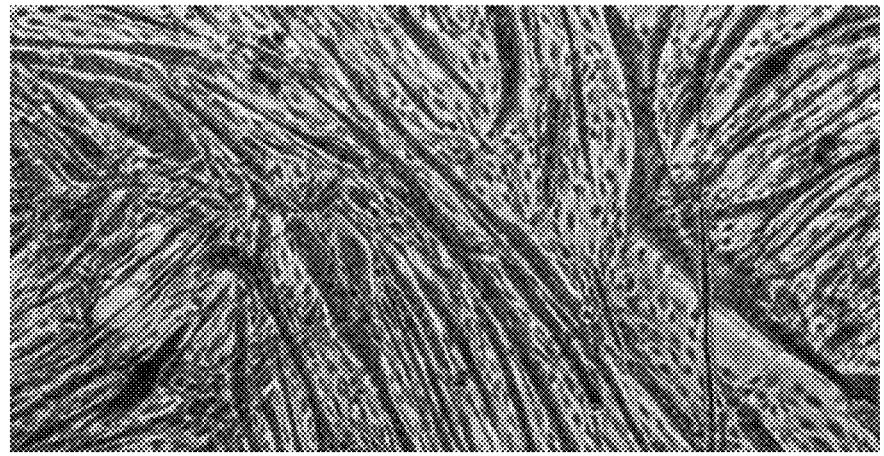
FIG. 1E  100 μm
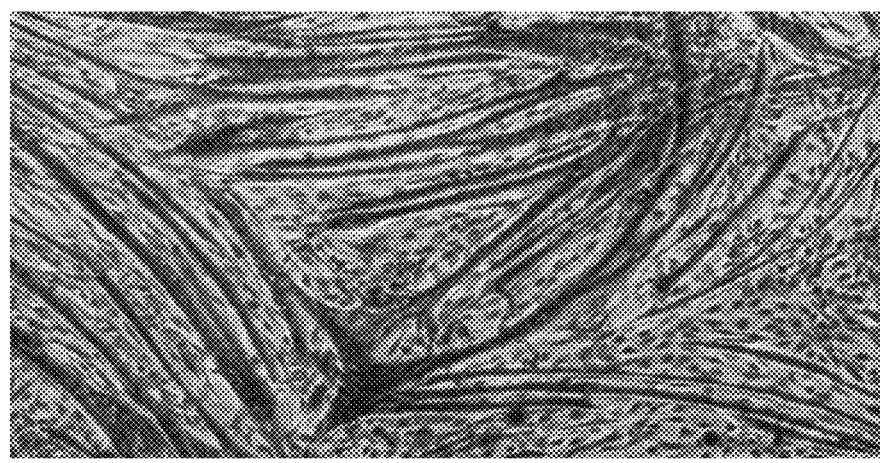
FIG. 1F  100 μm

METHOD FOR IMPROVING SARCOPENIA BY USING *PHELLINUS LINTEUS*

RELATED APPLICATION

This application claims priority to an earlier Taiwan Application Ser. No. 109136177, filed Oct. 19, 2020, which is incorporated herein by reference in its entirety.

BACKGROUND

Field of Invention

The present invention relates to a method of using *Phellinus linteus*. More particularly, the present invention relates to a method for improving sarcopenia by using *Phellinus linteus*.

Description of Related Art

Sarcopenia is one of the common diseases in older adults. The characteristics of sarcopenia include progressive and generalized loss of skeletal muscle mass and functions. If sarcopenia of a patient deteriorates, the activities and the quality of life of the patient decline. Moreover, the occurrence rates of other diseases, disability fall, and even death may increase.

The causes of sarcopenia include the degeneration of motor neurons, nutritional imbalance, a decrease of protein synthesis, chronic diseases and/or inflammation responses, etc. Until now, sarcopenia cannot be effectively controlled by pharmaceutical products, and thus can be delayed or proved only by exercising, managing the chronic diseases and/or the inflammation responses as well as taking certain nutrient.

*Phellinus linteus*, also called black hoof mushroom or "Sang Huang" in Chinese, is a medicinal mushroom belonging to the genus *Phellinus* in the family Hymenochaetaceae. *Phellinus linteus* grows on a trunk, especially the trunk of a plant belonging to Moraceae. *Phellinus linteus* has low toxicity but has many benefit effects, for example, anti-oxidation, anti-inflammatory, immunity enhancement, anti-cancer, liver protection, dementia prevention, cardiovascular disease prevention, anti-allergy (allergic rhinitis, eczema, rheumatoid arthritis), sleep improvement, analgesia (such as menstrual pain), inhibition of uric acid and skin maintenance, etc. However, at present, few studies have focused on whether *Phellinus linteus* has the effect on improving sarcopenia.

SUMMARY

Therefore, one aspect of the present invention provides a method for maintaining or delaying loss of muscle function and/or muscle mass of a subject in need thereof by using *Phellinus linteus* as an active ingredient to maintain the diameters of myotubes, muscle mass and muscular endurance.

According to the aforementioned aspect of the present invention, a method for maintaining muscle function and/or muscle mass in a subject in need thereof is provided, in which the method includes administering an effective dose of a composition including *Phellinus linteus* as an active ingredient to the subject. The *P. linteus* is deposited in National Institute of Technology and Evaluation (NITE), International Patent Organism Depositary (IPOD) on Nov. 12, 2020 with an accession number of NITE BP-03321 as well as deposited in Bioresource Collection and Research Center (BCRC) with an accession number of BCRC 930210. The aforementioned composition includes an extract of a fermented product of the *P. linteus* and/or its derivative.

In one embodiment of the present invention, the aforementioned extract of a fermented product can be obtained by performing a multistage incubation step and an extraction step on a first mycelium of the *P. linteus*, for example. First, a solid-state incubation step is performed on the first mycelium with a solid-state medium under 15° C. to 30° C. for 1 week to 2 weeks to obtain a second mycelium. Then, a liquid-state incubation step is performed on the second mycelium with a first liquid medium under 15° C. to 30° C. for 3 days to 14 days to obtain a third mycelium, in which a pH value of the first liquid medium is 2 to 6. Next, a ferment incubation step is performed on the third mycelium with a second liquid medium under 15° C. to 30° C. for 3 days to 21 days to obtain the fermented product of the *P. linteus*, in which a pH value of the second liquid medium is 2 to 6.

In one embodiment of the present invention, the extract of the fermented product can include a water extract of the fermented product and/or an ethanol extract of the fermented product, and the derivative can be selected from a group consisting of a desiccate of the water extract of the fermented product, a concentrate of the water extract of the fermented product, a desiccate of the ethanol extract of the fermented product, a concentrate of the ethanol extract of the fermented product and any combination thereof, for example.

In one embodiment of the present invention, the water extract of the fermented product is obtained by performing a water extraction step, and the water extraction step includes performing a hot water extract on the fermented product with 100° C. water.

In one embodiment of the present invention, the ethanol extract of the fermented product is obtained by performing an ethanol extraction step including an ultrasonic oscillation on the fermented product with ethanol.

In one embodiment of the present invention, the effective dose of the water extract of the fermented product for animal myocytes is 5 μg/mL to 15 μg/mL.

In one embodiment of the present invention, the effective dose of the ethanol extract of the fermented product for animal myocytes is 0.5 μg/mL to 1.5 μg/mL.

In one embodiment of the present invention, the effective dose of the active ingredient for a mouse is 400 mg/kilogram body weight (kg·bw)/day to 600 mg/kg·bw/day when the composition is administered to the mouse.

In one embodiment of the present invention, the effective dose of the active ingredient for a human is 2300 mg/kg·bw/day to 2500 mg/kg·bw/day when the composition is administered to the human.

In one embodiment of the present invention, the composition is a pharmaceutical composition or a food composition, and the composition further includes a food or pharmaceutical acceptable carrier, excipient, diluter, auxiliary, filler and/or additive.

Another aspect of the present invention provides a method for treating sarcopenia in a subject in need thereof, in which the method includes administering an effective dose of a composition comprising *Phellinus linteus* as an active ingredient to the subject. An accession number of the *P. linteus* is NITE BP-03321 and BCRC 930210, and the composition comprises an extract of a fermented product of the *P. linteus* and/or its derivative, in which the derivative can be selected from a group consisting of a desiccate of the water extract of the fermented product, a concentrate of the water extract of the fermented product, a desiccate of the ethanol extract of the fermented product, a concentrate of the ethanol extract of the fermented product and any combination thereof, for example.

In one embodiment of the present invention, the effective dose of the water extract of the fermented product for animal myocytes is 5 µg/mL to 15 µg/mL.

In one embodiment of the present invention, the effective dose of the ethanol extract of the fermented product for animal myocytes is 0.5 µg/mL to 1.5 µg/m L.

In one embodiment of the present invention, the effective dose of the active ingredient for a mouse is 400 mg/kilogram body weight (kg·bw)/day to 600 mg/kg·bw/day when the composition is administered to the mouse.

In one embodiment of the present invention, the effective dose of the active ingredient for a human is 2300 mg/kg·bw/day to 2500 mg/kg·bw/day when the composition is administered to the human.

By applying the method for maintaining muscle function and/or muscle mass in a subject in need thereof, in which the subject is subjected with the effective dose of a composition including *Phellinus linteus* as active ingredients, the diameters of myotubes as well as muscle mass and muscular endurance of a subject are maintained when the subject is administered with the composition.

BRIEF DESCRIPTION OF THE DRAWINGS

The invention can be more fully understood by reading the followed detailed description of the embodiment, with reference made to the accompanying drawings as follows:

FIGS. 1A to 1F showed microscopic photos of histological stains for mice skeleton muscular cells cultured by culture media with or without the extract of the fermented product and/or dexamethasone.

DETAILED DESCRIPTION

Figure 1A:

As mentioned above, the present invention provides method for maintaining muscle function and/or muscle mass in a subject in need thereof, in which the method includes administering an effective dose of a composition including *Phellinus linteus* as an active ingredient.

The aforementioned *P. linteus* can be the strain deposited in National Institute of Technology and Evaluation (NITE), International Patent Organism Depositary (IPOD) on Nov. 12, 2020 with an accession number of NITE BP-03321, as well as deposited in Bioresource Collection and Research Center (BCRC) on Jul. 18, 2019 with an accession number of BCRC 930210, in which the *P. linteus* is deposited in the form of mycelium. The deposit was made under the terms of the Budapest Treaty.

The mycelium of the aforementioned *P. linteus* is subjected to a multistage incubation step to obtain a fermented product of the *P. linteus*. Since *P. linteus* requires different culturing conditions (including nutrient and environmental factors) during different growing phases or differentiate phases, the multistage incubation step is required to control the culturing conditions at each growing stages of *P. linteus* to obtain more biomass and/or certain active ingredients.

In one embodiment, the multistage incubation step can include a solid-state incubation step, a liquid-state incubation step and a ferment incubation step. In details, the solid-state incubation step can be performed by culturing the mycelium (or called first mycelium) of the *P. linteus* with a solid-state medium to obtain a second mycelium, for example. The aforementioned solid-state medium can include carbon sources, nitrogen sources and other nutrients required for the growth of *P. linteus*. In one embodiment, the solid-state medium can be potato dextrose agar (PDA), for example. In one embodiment, the solid-state incubation step can be performed under 15° C. to 30° C. for 1 week to 2 weeks.

The second mycelium can be subjected to the aforementioned liquid-state incubation step with a first liquid medium, for example, to obtain a third mycelium, in which the pH value of the first liquid medium can be pH 2 to 6, for example, and the first liquid medium can include 1 weight % to 3 weight % mixed carbon-nitrogen resources (such as grains and/or beans), 1 weight % to 4 weight % sugar (such as monosaccharides and/or disaccharides), 0.1 weight % to 1 weight % yeast extract, 0.1 weight % to 1 weight % peptone and 0.01 weight % to 0.05 weight % inorganic salts (such as phosphate and/or sulfate). It should be understand that the ingredient of the aforementioned first liquid medium can be adjusted appropriately depending on the usage requirement. In one embodiment, the liquid-state incubation step is performed with the first liquid medium under 15° C. to 30° C. with a rotation speed of 110 rpm to 130 rpm for 3 days to 14 days.

The third mycelium can be subjected to the aforementioned ferment incubation step with a second liquid medium under 15° C. to 30° C. for 3 days to 21 days to obtain a fermented product, in which the ingredient of the second liquid medium can be same as the first liquid medium or can be adjusted according to the usage requirement, for example. The pH value of the second liquid medium can be 2 to 6, for example.

The aforementioned ferment incubation step can be performed in a fermenter, for example. In one embodiment, gases are introduced to the fermenter when the ferment incubation step is performed, in which the gases can be selected from a group consisting of air, oxygen, carbon dioxide, helium and any combination thereof, for example. In one example, the pressure of the gases in the fermenter can be 0.5 kg/cm$^2$ to 1.0 kg/cm$^2$, for example. In one embodiment, the ventilation rate can be 0.01 volume of gases introduced/volume of the second liquid medium/minute (VVM) to 1.5 VVM. In other embodiment, the rotation speed of the ferment incubation step is 50 rpm to 150 rpm.

Next, the aforementioned fermented product is subjected to an extraction step to obtain the extract of the fermented product. The extraction step can be performed with a known extraction method. In one embodiment, the fermented product is subjected to a solvent extraction by using a polar solvent to perform the extraction step, in which the polar solvent includes water and/or a lower alcohol (e.g., methanol, ethanol, 1-propanol, isopropanol, etc.). It is worth noting that in consideration to the requirement of the subsequent application, it is better to use water or ethanol for performing a water extraction or an ethanol extraction to obtain a water extract or an ethanol extract of the fermented product.

In one embodiment, the aforementioned water extraction can selectively be a hot-water extraction performed with boiled water (e.g., 90° C. to 100° C.). In another embodiment, the aforementioned ethanol extraction can be selectively combined with an ultrasonic oscillation, and be performed with 500 W to 700 W, 30 kHz to 50 kHz ultrasound under a room temperature (e.g., 10° C. to 40° C.). The time of the aforementioned extraction step is not limited. In one embodiment, the hot water extraction is performed for 20 minutes to 40 minutes. In other embodiment, the aforementioned ethanol extraction combined with an ultrasonic oscillation is performed for 40 minutes to 80 minutes to obtain a higher amount of active ingredient.

In the aforementioned embodiment, the weight ratio of the polar solvent to the extract of the fermented product is not limited, and can be 10 to 30, but not limited to the example herein.

In one embodiment, a reprocessing treatment can be optionally performed between the multistage incubation step and the extraction step, in which the reprocessing treatment can include but not be limited to a drying step and/or a concentration step for the sake of the subsequent extraction step.

The aforementioned drying step can be performed with a known drying method, such as a freeze-drying method, a vacuum drying method or a spray drying method. In one embodiment, the extract of the fermented product is subjected to a drying step to obtain a desiccate of the extract of the fermented product.

The aforementioned concentration step can be performed by a known concentration method, e.g., a reduced pressure concentration method, an evaporation concentration method or a membrane concentration method.

In one embodiment, the aforementioned reprocessing treatment can be included after the extraction step, to obtain derivatives of the extract of the fermented product. The aforementioned derivatives can be selected from a group consisting of the desiccate of the water extract of the fermented product, the concentrate of the water extract of the fermented product, the desiccate of the ethanol extract of the fermented product, the concentrate of the ethanol extract of the fermented product and any combination thereof.

The aforementioned extract of the fermented product and/or its derivatives are proved to have the effect of improving sarcopenia, thereby being applied to the preparation of a composition for improving sarcopenia. The "effect of improving sarcopenia" refers that the composition can maintain or delay loss of muscle function, muscle mass and/or muscular endurance of a subject in need thereof after the composition is administered to the subject. Specific indexes for the evaluation include being able to maintain the diameters of the myotubes, the muscle mass and muscular endurance.

Animal cell experiments have proved that the water extract and/or the ethanol extract of the fermented product can maintain the diameters of the myotubes effectively. In this embodiment, an effective dose of the water extract of the fermented product for animal muscular cells can be 5 μg/mL to 15 μg/mL, for example, and an effective dose of the ethanol extract of the fermented product for animal muscular cells can be 0.5 μg/mL to 1.5 μg/mL, for example. The water extract and the ethanol extract of the fermented product with amounts in the aforementioned range of effective dose are enough to delay sarcopenia effectively while being not toxic to the myocytes.

Moreover, evaluated by the animal experiment, the water extract and/or the ethanol extract of the fermented product are proved to be able to maintain the muscle mass and muscular endurance effectively.

In practice, the composition can include the extract of the fermented product and/or its derivative, and the dose of the extract of the fermented product and/or its derivative can be determined based on their dosage forms and the subject to be administered. In one embodiment, the effective dose of the water extract of the fermented product and/or the ethanol extract of the fermented product can be 400 mg/kilogram body weight (kg·bw)/day to 600 mg/kg·bw/day, for example, when the composition is administered to a mouse. In one embodiment, the effective dose of the water extract and/or the ethanol extract of the fermented product can be 2300 mg/60 kg·bw/day to 2500 mg/60 kg·bw/day, for example, when the composition is administered to a human.

In practice, the aforementioned composition can be a food composition or a pharmaceutical composition. In one embodiment, the composition can selectively include a food or a pharmaceutical acceptable carrier, excipient, diluter, auxiliary, filler and/or additive.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the followed claims.

Example 1. Preparation of Fermented Product and its Derivatives of *Phellinus linteus*

The first mycelium of *P. linteus* in EXAMPLE 1 was deposited in the International Patent Organism Depositary (IPOD) of the independent administrative corporation, National Institute of Technology and Evaluation (NITE) (Address of depositary institution: Chuo Dai-6, 1-1 Higashi 1-Chome, Tsukuba-shi, Ibaraki-ken, Japan) on Nov. 12, 2020 with an accession number of NITE BP-03321. The first mycelium of *P. linteus* was also deposited in Bioresource Collection and Research Center (BCRC) at the Food Industry Development and Development Institute (FIRC) (address: No. 331 on Shih-Pin Road, Hsinchu, Taiwan) on Jul. 18, 2019 with an accession number of BCRC 930210. The strain was separated from a fruit body of a wild *P. linteus* found in China.

Please referred to the Taiwan Patent TW 1729928 B (application no. TW 109129939A) for the microorganism traits and the culturing method of the *P. linteus* (NITE BP-03321 and BCRC 930210). The patent was cited as a reference herein.

The mycelium of the *P. linteus* (also called a first mycelium) deposited in NITE or BCRC was inoculated on potato dextrose agar (PDA) and was cultured under 25° C. for 7 days to obtain a second mycelium. Then, a portion of the second mycelium of the *P. linteus* was scraped and picked to be inoculated on a first liquid medium, followed by a culture step performed under 25° C., pH 5, a rotation speed of 120 rpm for 7 days to obtain a third mycelium, in which the aforementioned first liquid medium included 1 weight % mixed carbon-nitrogen resources, 1.5 weight % sugar, 0.3 weight % yeast extract, 0.3 weight % peptone and 0.05 weight % inorganic salts. The aforementioned mixed carbon-nitrogen resources were grains (flour and/or bran powder) and/or beans (soybean powder, green bean powder and/or cinnamon powder). The aforementioned sugar was monosaccharides (glucose and/or fructose) and/or disaccharides (maltose and/or sucrose). The aforementioned inorganic salts were phosphate (dipotassium hydrogen phosphate and/or potassium dihydrogen phosphate) and/or sulfate (magnesium sulfate and/or iron sulfate). The specific ingredients of the mixed carbon-nitrogen resources, sugars and inorganic salts were well-known to a person having ordinary skill in the art and could be arbitrarily adjusted according to the specific need without affecting the fermentation step, and thus would not be elaborated herein.

Next, a portion of the third mycelium of *P. linteus* in the first liquid medium was inoculated into a second liquid medium (with the ingredient same as the first liquid medium) in a fermenter, followed by fermentation at 25° C., pH 5 with a pressure of 0.5 kg/cm$^2$, a ventilation rate of 1.0 VVM and a stirring rate of 80 rpm for 14 days to obtain a fermented product.

The fermented product was subjected to a freeze-drying to obtain a lyophilized powder of the fermented product. In the example, 3 kg lyophilized powder of the fermented product could be obtained from 100 L fermented product.

Then, the lyophilized powder of the fermented product was subjected to an extraction step to obtain an extract of the fermented product, in which the extract of the fermented product included a water extract and an ethanol extract of the fermented product. The aforementioned water extract of the fermented product was obtained by performing a hot water extract with 100° C. distilled water for 30 minutes, in which the weight ratio of water to the lyophilized powder of the fermented product was 20. The water extract of the fermented product was subjected to a lyophilization after cooling to a room temperature to obtain Sample 1.

The aforementioned ethanol extract of the fermented product was obtained by performing an ultrasonic oscillation with ethanol index 25° C. for 1 hour, in which the ultrasonic oscillation was performed with 600 W, 40 kHz ultrasonic waves and ethanol by an ultrasonic cleaner (maker: Delta Ultrasonic Co., Ltd, Taiwan; Cat: #DC600H), and the weight ratio of ethanol to the lyophilized powder of the fermented product was 20. Then, a centrifuge was performed for separation, in which the supernatant was the ethanol extract of the fermented product. Then, a reduced pressure concentration method was performed on the ethanol extract of the fermented product to obtain Sample 2.

The Sample 1 and the Sample 2 were dissolved in dimethyl sulfoxide (DMSO) to for the subsequent preparation.

Example 2. Determination of the Effect of the Extract of the Fermented Product on Maintaining Diameters of the Myotubes, the Muscle Mass and Muscular Endurance Mouse skeletal myocytes (i.e., C2C12 cell line) were utilized to establish a sarcopenia model. An artificially synthetic corticosteroid, dexamethasone was utilized to establish the sarcopenia model. Dexamethasone could inhibit the immune system and thus was utilized as an anti-inflammation drug or an allergy drug. However, dexamethasone also had side effects such as muscular dystrophy (including the decrease of the muscle mass and/or the decrease of the muscular endurance). Thus, dexamethasone was used to induce muscular dystrophy for simulating sarcopenia in this Example.

First, a growth medium [Dulbecco's modified minimal essential medium (DMEM) including 10% fetal bovine serum] was utilized to culture the C2C12 cell line under 37° C., 5% $CO_2$, in which the start density of the C2C12 cell line was $1 \times 10^5$ to $2 \times 10^5$ cells/mL. When the C2C12 cell line had grown to 70% confluence, a differentiate medium (the DMEM including 2% horse serum) was used to perform a differentiation culture for 7 day to obtain differentiated cells, in which 90% differentiated cells were converted into myotubes, and the differentiation culture was changed once every 2 days during the 7 days.

Next, the aforementioned differentiated cells were divided into a blank control group, a negative control group, an experimental group 1, an experimental group 2, an experimental group 3 and an experimental group 4, in which the medium of the blank control group was DMEM including 0.1% DMSO, the medium of the negative control group was DMEM including 0.1% DMSO and 10 µM dexamethasone, the medium of the experimental group 1 was DMEM including 10 µg/mL Sample 1, the medium of the experimental group 2 was DMEM including 10 µM dexamethasone and 10 µg/mL Sample 1, the medium of the experimental group 3 was DMEM including 1 µg/mL Sample 2, and the medium of the experimental group 4 was DMEM including 10 µM dexamethasone and 1 µg/mL Sample 2. It was worth noting that Sample 1 and Sample 2 were dissolved in the DMSO before being used to prepare the media, and the media of the experimental group 1 to the experimental group 4 contained DMSO, but the DMSO at concentrations less than or equal to 0.1% showed less toxicity to cells.

Figure 1B:
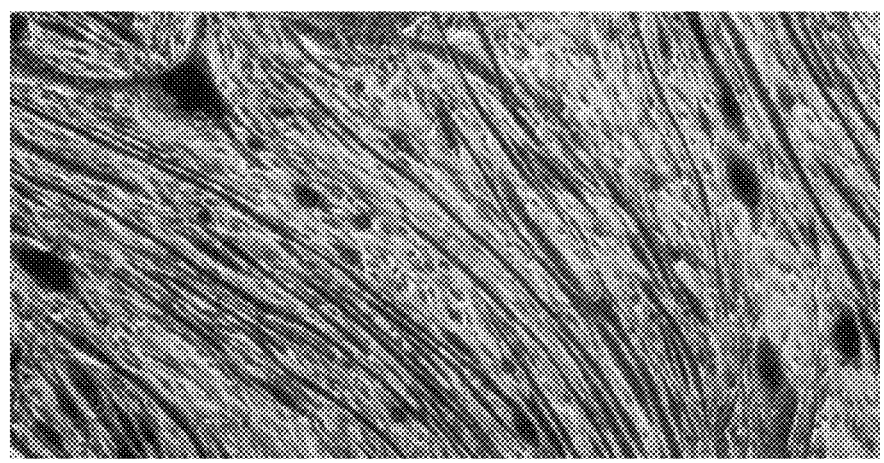

After the aforementioned differentiated cells were cultured under 37° C., 5% $CO_2$ for 24 hours using the aforementioned media, hematoxylin and eosin (H&E) stain was performed, and then the diameters of the myotubes of the differentiated cells were observed by an optic microscope, as shown in FIGS. 1A to 1F.

FIGS. 1A to 1F showed microscopic photos of histological stains for mice skeleton muscular cells cultured by culture media with or without the extract of the fermented product and/or dexamethasone, in which FIGS. 1A to 1F were corresponding to the blank control group, the negative control group, the experimental group 1, the experimental group 2, the experimental group 3 and the experimental group 4. Compared to FIG. 1A (the blank control group), the diameters of the myotubes shown in FIG. 1B (the negative control group) were smaller, but compared to FIG. 1B (the negative control group), the diameters of the myotubes shown in FIGS. 1C to 1F (the experimental group 1 to the experimental group 4) were bigger.

The diameters of the myotubes were measured by using a commercial software (Image-Pro Plus software), and the results of statistical analysis on the diameters of the myotubes were shown in Table 1, in which the statistic method used to analyze the percentage of each items was paired sample t-test, and the symbols "#" and "*" represented significant differences compared to the blank control group and negative control group ($p<0.05$, $n=60$), respectively.

TABLE 1

| Group | Diameters of the myotubes (µm) |
|---|---|
| Blank control group | 30.39 ± 4.52 |
| Negative control group | 19.98 ± 6.42# |
| Experimental group 1 | 25.20 ± 6.14* |
| Experimental group 2 | 29.90 ± 6.67* |
| Experimental group 3 | 27.14 ± 6.97* |
| Experimental group 4 | 30.06 ± 5.55* |

As shown in Table 1, the diameters of the myotubes of the negative control group significantly decreased compared to the blank control group, indicating that dexamethasone could exactly lead to muscular dystrophy. However, the diameters of the myotubes of the experimental group 2 and the experimental group 4 were significantly higher than that of the negative control group, indicating that the water extract and/or the ethanol extract of the fermented product could maintain the diameters of the dexamethasone-induced myotubes, suggesting that the water extract and/or the ethanol extract of the fermented product could delay and/or avoid the loss of the muscle mass. Besides, there was no statistically significant difference between the experimental group 1 as well as the experimental group 3 and the blank control group, indicating that the water extract and/or the ethanol extract of the fermented product were not toxic to the myotubes cells.

Example 3. Evaluation of Effect of Extract of the Fermented Product on Maintaining Muscle Mass and Muscular Endurance Equal weights of the aforementioned Sample 1 and Sample 2 were mixed to obtain Sample 3.

C57BL/6J mice were utilized as the model animal in this example. The mice were divided into a blank group, a control group and an experimental group, and the mice in each groups were treated with the corresponding test samples by oral gavage once a day, in which the test sample for the experimental group was Sample 3, and the test samples for the blank control group and the control group were water. Specifically, Sample 3 was dissolved in an adequate amount of water and the treating amount was controlled at 500 mg/kg·bw/time, and the volumes of water administered to the mice of the blank group and the control group were equal to the total volume of the mixture of Sample 3 and water.

The hind limbs of the mice in the experimental group and the control group were subjected to a cast immobilization treatment for 7 days to induce the hind limbs of the mice to become atrophy. Then, the mice were allowed to move around freely in mice cages for 7 days after the casts were removed. Then, a muscular endurance experiment was performed to measure the skeleton muscles of the hind limbs of the mice. After that, the mice were sacrificed. The mice were continued to be treated by oral gavage with the corresponding test samples for total 14 days during the cast immobilization treatment and the period that the mice were allow to move around freely.

In the aforementioned muscular endurance experiment, each mouse was placed on a treadmill with an inclination, in which a conveyor belt of the treadmill was set at a speed of 18 m/minute to 20 m/minute downward, and a shock grid was positioned at the end of the treadmill. If a mouse kept in a stationary position, the mouse would be pushed by the moving conveyor belt to the bottom of the treadmill that provided the tail of the mouse with and electrical shock. In general, the mouse would run upward to avoid the tail from being electrically shocked. However, the mouse lacking muscular endurance could not run faster than the speed of the conveyor belt, so that it would be pushed to the bottom of the treadmill and provided with an electrical shock. During the same time, the more times the mouse were electrically shocked, the worse the muscular endurance of the mouse were. The commercial software GraphPad Prism (version 8.0) were utilized to analyzed the times that the mice got electrically shocked with one-way ANOVA followed by Dunnett's test as the post-hoc test. The results were show in Table 2, in which the symbols of "#" and "*" represented significant differences compared to the blank group and the control group ($p<0.05$, $n=60$), respectively.

TABLE 2

| Group | Times of the electric shock |
| --- | --- |
| Blank group | 3.00 ± 2.28 |
| Control group | 500.83 ± 257.37# |
| Experimental group | 25.60 ± 48.87* |

As shown in Table 2, the times of the electric shocks on the mice of the control group were significantly increased compared to the blank group, indicating that the cast immobilization treatment could exactly cause muscle atrophy and the loss of the muscular endurance of the mice. However, the times of the electric shocks on the mice in the experimental group were significantly decreased compared to the control group, indicating that administering the mixture of the water extract and the ethanol extract of the fermented product could effectively maintain the muscle mass and muscular endurance, thereby delaying and/or avoiding the loss of the muscular endurance of the mice.

Next, the mice were sacrificed, and the weights of the gastrocnemius muscles in the hind limbs of the mice were measured. The results were analyzed with one-way ANOVA followed by Dunnett's test as the post-hoc test for the differences between groups. The results were shown in Table 3, in which the relative weight was the weight of the gastrocnemius muscles divided by the weight of the mouse to exclude the factors of individual differences on size, and the symbols of "#" and "*" represented statistically significant differences compared to the blank group and the control group ($p<0.05$, $n=60$), respectively.

TABLE 3

| Group | Relative weight (mg/g) |
| --- | --- |
| Blank group | 5.485 ± 0.234 |
| Control group | 4.895 ± 0.384# |
| Experimental group | 5.051 ± 0.182* |

As shown in Table 3, the relative weights of the gastrocnemius muscles of the control group were significantly lower than that of the blank group, indicating that the cast immobilization treatment could result in the decline of the muscle mass. However, the relative weight of the gastrocnemius muscles of the experimental group were significantly higher than that of the control group, indicating that administering the mixture of the water extract and the ethanol extract of the fermented product could effectively maintain the muscle mass, thereby delaying and/or avoiding the loss of the muscle mass.

Example 4. Estimation of the Effective Dose for Human Body

According to the estimating method for initial clinical trials announced by Food and Drug Administration (FDA) on 2005, the effective dose for human body was estimated by the effective dose for mice. The effective dose per kilogram of body weight (kg·bw) for human body was estimated by dividing the effective dose per kilogram of body weight for mice with the coefficient 12.3. Based on the result that the mouse was administered daily with 500 mg/kg·bw in the above examples, the effective dose equivalent to human body was 2400 mg/60 kg·bw/day, in which the average adult human body weight was 60 kg.

In sum, the water extract and the ethanol extract of the fermented product of the *P. linteus* of the present invention can effectively maintain the diameters of the myotubes, the muscle mass and the muscular endurance, and thus can be utilized to improve sarcopenia.

Noting that although the specific process, the specific analysis method and/or the specific instruments are shown in the present invention as examples to explain the method of improving sarcopenia in a subject in need thereof, it will be apparent to those skilled in the art that the present invention is not limited to what have mentioned. Without departing from the scope or spirit of the invention, it is intended that other strains, other process, other analysis method or other instruments can also explain the present invention.

Although the present invention has been described in considerable detail with reference to certain embodiments thereof, other embodiments are possible. Therefore, the spirit and scope of the appended claims should not be limited to the description of the embodiments contained herein.

What is claimed is:

1. A method for treating sarcopenia in a subject in need thereof, comprising:

administering a composition comprising an effective dose of an extract of a fermented product of *Phellinus* linteus and/or its derivative as an active ingredient to the subject, wherein the Phellinus linteus is deposited in National Institute of Technology and Evaluation (NITE), International Patent Organism Depositary (IPOD) on November, 12th, 2020 with an accession number of NITE BP-03321, the extract comprises a water extract and/or an ethanol extract, the water extract is obtained by performing a water extraction step at 90° C. to 100° C. on the fermented product for 20 minutes to 40 minutes, and the ethanol extract is obtained by performing an ethanol extraction step at 10° C. to 40° C. on the fermented product for 40 minutes to 80 minutes combining with an ultrasonic oscillation with an ultrasound of 500 W to 700 W, 30 kHz to 50 kHz.

2. The method for treating sarcopenia in the subject in need thereof of claim 1, wherein the subject is an animal myocyte, and the effective dose of the water extract of the fermented product is 5 μg/mL to 15 μg/mL.

3. The method for treating sarcopenia in the subject in need thereof of claim 1, wherein the subject is an animal myocyte, and the effective dose of the ethanol extract of the fermented product is 0.5 μg/mL to 1.5 μg/mL.

4. The method for treating sarcopenia in the subject in need thereof of claim 1, wherein the subject is a mouse, and the effective dose is 400 mg/kilogram body weight (kg.bw)/day to 600 mg/kg.bw/day.

5. The method for treating sarcopenia in the subject in need thereof of claim 1, in which wherein the subject is a human, and the effective dose is 2300 mg/kg.bw/day to 2500 mg/kg.bw/day.

6. The method for treating sarcopenia in the subject in need thereof of claim 1, wherein the derivative is selected from a group consisting of a desiccate of the water extract of the fermented product, a concentrate of the water extract of the fermented product, a desiccate of the ethanol extract of the fermented product, a concentrate of the ethanol extract of the fermented product and any combination thereof.

7. The method for treating sarcopenia in the subject in need thereof of claim 1, wherein the extract of the fermented product of the Phellinus linteus is obtained by performing a multistage incubation step and an extraction step on a first mycelium of the Phellinus linteus, and the multistage incubation step includes:

performing a solid-state incubation step on the first mycelium with a solid-state medium under 15° C. to 30° C. for 1 week to 2 weeks to obtain a second mycelium;

performing a liquid-state incubation step on the second mycelium with a first liquid medium under 15° C. to 30° C. for 3 days to 14 days to obtain a third mycelium, in which a pH value of the first liquid medium is 2 to 6; and performing a ferment incubation step on the third mycelium with a second liquid medium under 15° C. to 30° C. for 3 days to 21 days to obtain the fermented product of the Phellinus linteus, in which a pH value of the second liquid medium is 2 to 6.

8. The method for treating sarcopenia in the subject in need thereof of claim 1, wherein compared to a control subject not administered to the extract of the fermented product of the Phellinus linteus and/or its derivative, the subject administered to the extract of the fermented product of the Phellinus linteus and/or its derivative has an increased diameters of myotubes.

* * * * *